United States Patent [19]

Schumacher et al.

[11] 4,426,543

[45] Jan. 17, 1984

[54] VAPOR PHASE NITRATION OF AROMATIC HYDROCARBONS

[75] Inventors: Ignatius Schumacher, Ballwin; Kang-Bo Wang, Creve Coeur, both of Mo.

[73] Assignee: Monsanto Company, St. Louis, Mo.

[21] Appl. No.: 349,487

[22] Filed: Feb. 17, 1982

Related U.S. Application Data

[63] Continuation-in-part of Ser. No. 210,423, Nov. 26, 1980, abandoned.

[51] Int. Cl.$^3$ .............................................. C07C 79/10
[52] U.S. Cl. ..................................... 568/940; 568/939
[58] Field of Search ............... 568/932, 934, 935, 939, 568/940

[56] References Cited

U.S. PATENT DOCUMENTS

| | | |
|---|---|---|
| 2,109,873 | 3/1938 | Wilhelm .............................. 260/142 |
| 2,431,585 | 11/1947 | Rout ..................................... 260/645 |
| 3,966,830 | 6/1976 | Shimada et al. .................... 260/646 |
| 4,107,220 | 8/1978 | Owsley et al. ...................... 260/646 |
| 4,112,006 | 9/1978 | Schubert et al. .................... 260/645 |
| 4,123,466 | 10/1978 | Lin et al. ............................. 568/940 |

OTHER PUBLICATIONS

McKee et al., Industrial and Engineering Chemistry, vol. 28, (1958), pp. 662–667.

Primary Examiner—Leland A. Sebastian
Attorney, Agent, or Firm—Wendell W. Brooks; James C. Logomasini; Arnold H. Cole

[57] ABSTRACT

Aromatic hydrocarbons selected from the group consisting of benzene and toluene are nitrated in the vapor phase at temperatures between about 80° C. and about 190° C. in the presence of a molecular sieve catalyst.

15 Claims, No Drawings

VAPOR PHASE NITRATION OF AROMATIC HYDROCARBONS

This application is a continuation-in-part of our copending application Ser. No. 210,423, filed Nov. 26, 1980, now abandoned.

BACKGROUND OF THE INVENTION

1. Field of the Invention

This invention relates to a process for the nitration of aromatic hydrocarbons. More particularly, this invention relates to a process for the vapor phase nitration of aromatic hydrocarbons selected from the group consisting of benzene and toluene in the presence of a molecular sieve catalyst.

Nitrated aromatic hydrocarbons find use as solvents, explosives, dyes, perfumes, and analytical reagents, and are important as intermediates in organic synthesis. As an example, nitrated aromatic hydrocarbons are convertible by reduction into primary amines, which, in turn, are valuable intermediates in the synthesis of dyes, pharmaceuticals, photographic developers, antioxidants, and gum inhibitors.

2. Description of the Prior Art

Vapor phase nitration of aromatic hydrocarbons is known in the art. The vapor phase nitration of benzene and toluene at temperatures ranging from about 275° C. to about 310° C. is described in McKee and Wilhelm, *Industrial and Engineering Chemistry*, 28(6), 662-667 (1936) and U.S. Pat. No. 2,109,873. McKee and Wilhelm catalyzed their reaction with silica gel, with best results being reported by the use of 14 mesh material. Bauxite and alumina were reported to be ineffective as catalysts in the vapor phase nitration of benzene. U.S. Pat. No. 2,431,585 describes a vapor phase nitration of aromatic hydrocarbons at temperatures from 130° C. to 430° C. in the presence of a catalyst selected from the group consisting of metal metaphosphates, boron phosphate, and solid and supported phosphoric acid catalysts. Preferred catalysts are the metal metaphosphates such as those of calcium, iron, and magnesium. More recently, U.S. Pat. No. 4,112,006 described a process for nitrating toluene in the vapor phase in the presence of an acidic inorganic catalyst consisting of a carrier substance based on silica and/or alumina impregnated with a high boiling inorganic acid such as sulfuric acid or phosphoric acid and, optionally, with metal salts of such acids. The reaction is run under reduced pressure at temperatures from about 80°-180° C., with 100° C. to 140° C. being preferred.

The use of molecular sieve catalysts having a pore size varying from about 5 Å to about 10 Å is described in U.S. Pat. No. 4,107,220 as an effective catalyst for controlling the para/ortho isomer distribution of nitrochlorobenzene during the vapor phase nitration of chlorobenzene. A suitable temperature range was reported to be from about 190° C. to about 290° C.

Although these prior art processes for the vapor phase nitration of aromatic hydrocarbons generally provide the desired product, they nevertheless are limited in their applications. Principal among these limitations are low (aromatic hydrocarbon) conversions and contamination of the nitrated aromatic hydrocarbon product by undesirable by-products and the complicated nature of the catalysts.

SUMMARY OF THE INVENTION

This invention is directed to a process for the vapor phase nitration of aromatic hydrocarbons selected from the group consisting of benzene and toluene in the presence of a molecular sieve catalyst. Accordingly, typical objects of the invention are to provide a relatively low-temperature vapor phase process for the preparation of nitrated aromatic hydrocarbons and to provide a vapor phase nitration process for converting aromatic hydrocarbons selected from the group consisting of benzene and toluene to the corresponding nitrated aromatic hydrocarbons characterized by high aromatic hydrocarbon conversion and high nitrated aromatic hydrocarbon selectivity.

These and other objects, aspects, and advantages of the invention will become apparent to those skilled in the art from the accompanying description and claims.

The above objects are achieved by the process disclosed herein for the vapor phase nitration of aromatic hydrocarbons selected from the group consisting of benzene and toluene which comprises contacting the aromatic hydrocarbon with a nitrating agent in the vapor phase in the presence of a molecular sieve catalyst at temperatures between about 80° C. and about 190° C.

DESCRIPTION OF THE PREFERRED EMBODIMENTS

In accordance with this invention, aromatic hydrocarbons selected from the group consisting of benzene and toluene are nitrated in the vapor phase by a process which comprises contacting the aromatic hydrocarbon with a nitrating agent in the vapor phase in the presence of a molecular sieve catalyst at a temperature between about 80° C. and about 190° C. The process is characterized by high aromatic hydrocarbon conversion and high nitrated aromatic hydrocarbon selectivity.

Aromatic hydrocarbons suitable for use in the present process are those selected from the group consisting of benzene and toluene. Such compounds are susceptible of existing in the vapor phase at temperatures less than about 190° C. (at atmospheric pressures). It has been found, however, that the process of this invention is particularly efficacious with benzene.

The nitrating agents which are employed in the process of this invention are the gaseous oxides of nitrogen higher than nitric oxide (NO) such as nitrogen dioxide ($NO_2$), dinitrogen trioxide ($N_2O_3$), and dinitrogen tetroxide ($N_2O_4$). Of these nitrating agents, nitrogen dioxide is preferred. Thus, for convenience and clarity the process will be described with reference to the preferred nitrogen dioxide as the nitrating agent.

The molecular sieve catalyst employed in accordance with this invention are aluminosilicate compounds having a well-defined crystalline structure; they may or may not be hydrated. The fundamental structural units are silicon and aluminum atoms tetrahedrally coordinated with four oxygen atoms. The silicate and aluminate units are generally joined to form 4- and 6-membered rings of oxygen atoms forming a simple and consistent arrangement of polyhedra. Each polyhedra is a three-dimensional array of tetrahedra in a definite geometric form.

The pore size of the molecular sieve catalyst suitable for use in the present process is not narrowly critical. However, the pore size preferably should be at least 5 Å. The use of a substantially smaller pore size molecular sieve has been found to have substantially reduced effectiveness for producing the nitrated aromatic hydrocarbon under conditions employed herein to produce the desired product. The maximum pore size of the molecular sieve is not critical and is limited only in terms of practicality and the availability of such molecular sieves.

Illustrative examples of the structure and synthesis of conventional molecular sieve catalysts suitable for use in this invention can be had by reference to U.S. Pat. Nos. 2,882,243; 2,882,244; 3,130,007; and 3,216,789; all of which are incorporated herein by reference. For further information thereon and a general review of zeolite molecular sieve catalysts, see Breck, *Zeolite Molecular Sieves*, John Wiley & Sons, New York, NY 1974.

Representative examples of suitable molecular sieve catalysts are analcime, bikataite, brewsterite, chabazite, clinoptilobite, bachiardite, edingtonite, epistilbite, erionite, faujasite, ferrierite, gismondine, gmelinite, gonnardite, harmontome, heulandite, kieselguhr, laumontite, levynite, losod, mesolite, mordenite, natrolite, omega, paulingite, phillipsite, scolecite, sodalite hydrate, stilbite, thomsonite, yugawaralite, and those compounds known as "A", "N-A", "L$^h$", "P", "T", "X", "Y", "ZK-4", and "ZK-5".

Of these molecular sieve catalysts, mordenite is preferred. Some commercially available mordenite molecular sieve catalysts are:

Zeolon 900H (8-9 Å pore size; $SiO_2/Al_2O_3$ molar ratio—10/1) from Norton Company; and Zeolon 200H (8-9 Å pore size; $SiO_2/Al_2O_3$ molar ratio—10/1) from Norton Company.

It will be appreciated that the invention is not limited to the aforesaid specific molecular sieves and that other suitable molecular sieves having larger and smaller pore size dimensions as well as larger and smaller $SiO_2/Al_2O_3$ molar ratios can be readily selected by persons skilled in the art in light of the aforesaid disclosures and the specific illustrative examples.

In a preferred embodiment the molecular sieve catalyst is conditioned by pretreatment with nitrogen dioxide at operating conditions to the saturation point (in the absence of the aromatic compound). Pretreatment times in general range from about 1 minute to about 1 hour or more. The actual pretreatment time, however, will depend upon the amount or quantity and pore structure of the molecular sieve catalyst, the flow rate of the nitrogen dioxide, the operating conditions, and the like. Usually, pretreatment for about 5 minutes to about 30 minutes is sufficient.

The conditioning pretreatment, while not absolutely necessary, is preferred because it permits almost immediate production of the nitrated aromatic hydrocarbon upon introduction of the aromatic hydrocarbon to the reactor. In the absence of the pretreatment, measurable nitrated aromatic hydrocarbon production is delayed until the molecular sieve catalyst becomes saturated with nitrogen dioxide.

The vapor phase nitration process of this invention is conducted at temperatures between about 80° C. and about 190° C., with temperatures between about 150° C. and about 175° C. being preferred in that at such preferred temperatures the rate of reaction is reasonably rapid and little, if any, by-product formation occurs. It will be appreciated, however, that the particular temperatures employed for a given aromatic hydrocarbon will depend to some extent upon the boiling point or vaporization temperature of the particular aromatic compound. For example, when toluene which has a boiling point of 110° C. is the aromatic hydrocarbon of choice, the vapor phase nitration is conveniently carried out at temperatures of at least 110° C., preferably within the aforesaid preferred temperature range, with 175° being particularly preferred. When benzene (b.p., 80° C.) is the aromatic hydrocarbon of choice, the vapor phase nitration may be conducted at temperatures which encompass the entire operative temperature range, that is, from about 80° to about 190° C. Again, however, temperatures between about 150° C. and about 175° C. are preferred.

The advantages accruing from conducting the vapor phase nitration of this invention at the relatively low elevated temperatures between about 80° C. and about 190° C. include:

(a) greater selectivity to the desired nitrated aromatic hydrocarbon;
(b) little, if any, by-product formation (to contaminate the desired product);
(c) high material balance between reactants and products;
(d) lower energy requirements; and
(e) minimal thermal decomposition of the nitrogen dioxide.

The latter advantage [(e)] is particularly significant in that it, to a large extent, influences the remaining advantages. It, of course, is well-known in the art that at elevated temperatures nitrogen dioxide undergoes thermal decomposition into the inert (for purposes of this invention) nitric oxide and molecular oxygen. The decomposition begins at about 150° C. and is complete at about 620° C. The decomposition at various temperatures is as follows:

| Temperature, °C. | 130 | 150 | 184 | 279 | 494 | 620 |
|---|---|---|---|---|---|---|
| Decomposition, % | 0 | 3 | 5 | 13 | 56.5 | 100 |

Thus, at temperatures between about 80° C. and about 190° C., the maximum loss of active nitrogen dioxide by thermal decomposition into inert nitric oxide is only about 5%, while at higher temperatures up to about 300° C., the loss by thermal decomposition rapidly increases to 20-30% or more. Clearly, the magnitude of the loss of nitrogen dioxide at temperatures higher than the operating temperatures of this invention is wasteful and impractical. Moreover, if recirculation of the effluent stream from such high temperature processes is desired, it is necessary to employ an additional step to reoxidize the inert nitric oxide to the active nitrogen dioxide by treatment thereof with oxygen or an oxygen-containing gas such as air, with the attendant added cost and complexity. The additional cost and complexity of this added step, however, is substantially reduced or eliminated altogether by the relatively low temperature conditions employed in the process of this invention.

The vapor phase nitration process of this invention is carried out in the presence of water, which is believed necessary to create and renew reaction sites on the molecular sieve catalyst. The required water can be supplied by water of hydration in the molecular sieve catalysts or, alternatively, by the separate addition of water via the feed stream. When water of hydration is present, no added water is required since once the reaction is initiated, water produced during the course of the reaction (1 mole of water for each 2 moles of nitrated aromatic hydrocarbon produced) is sufficient to sustain it. If the molecular sieve catalyst is substantially anhydrous, it then becomes necessary to add water in an amount sufficient to provide the required reaction sites. The separate addition of water is usually preferred to ensure its presence in sufficient amounts. The amount of water present, however, is not narrowly critical. Thus, amounts ranging from nominal or trace amounts up to about 15% by volume of the feed stream are generally sufficient, with amounts ranging from about 0.5% to about 5% by volume being desirably used.

The vapor phase nitration of this invention is conveniently carried out in an apparatus of the type suitable for carrying out chemical reactions in the vapor phase. It can be conducted in a single reactor or in multiple reactors using either a fixed bed, moving bed, or a fluidized bed system to effect contacting of the reactants and the molecular sieve catalyst. The reaction is generally carried out by continuously passing a vaporous mixture of the aromatic hydrocarbon and nitrogen dioxide over a bed of the molecular sieve catalyst while maintaining a temperature between about 80° C. and about 190° C., and usually, about 150° C. to about 175° C.

The reactant aromatic hydrocarbon can be preheated to form a vapor which is then admixed with gaseous nitrogen dioxide in a suitable reactor in predetermined relative proportions. Vaporous aromatic hydrocarbons can be conveniently swept into the reactor at a constant rate by a water-containing stream of carrier gas and thence admixed with a continuous stream of nitrogen dioxide before contacting the heated catalyst bed. The reactants can be charged into the reactor at any suitable flow rate.

As previously indicated, the reactant materials are conveniently swept into the reactor by a stream of carrier gas. The carrier gas employed in the present process can be oxygen or an oxygen-containing gas, for example, air, or an inert gas such as nitrogen, helium, and the like. It is advantageous, however, to employ oxygen or an oxygen-containing gas as the carrier gas due to the stoichiometry of the nitration reaction between the aromatic hydrocarbon and the nitrogen dioxide.

In the initial nitration reaction between the aromatic hydrocarbon and the nitrogen dioxide, it is believed that for each 2 moles of aromatic hydrocarbon, 3 moles of nitrogen dioxide are required to produce 2 moles of nitrated aromatic hydrocarbon, 1 mole of nitric oxide, and 1 mole of water. In the absence of an oxygen source such as supplied by the oxygen-containing carrier gas, the nitric oxide is lost, thereby reducing the nitrogen dioxide selectivity to the nitrated aromatic hydrocarbon by at least 33% (one-third), as well as the material balance between reactants and recovered products. In the presence of oxygen (and the molecular sieve catalyst), however, the nitric oxide undergoes the known reoxidation to nitrogen dioxide (stoichiometrically requiring 1 mole of oxygen for each 2 moles of nitric oxide), which undergoes further reaction with additional aromatic hydrocarbon. Overall, therefore, little, if any, nitrogen dioxide is lost by virtue of stoichiometrically produced nitric oxide.

The concentration of the aromatic hydrocarbon in the feed mixture is not narrowly critical. All that is necessary is that the concentration be sufficient to permit the reaction to proceed at a reasonable rate. On the other hand, since the nitrated aromatic hydrocarbon produced will have a high vaporization temperature (in fact, higher than the operating temperature range, for example, nitrobenzene, b.p. 210° C.), the concentration should be such that the nitrated aromatic hydrocarbon produced will not condense in the reactor. In addition, since mixtures of aromatic hydrocarbons and air (the preferred aromatic hydrocarbon carrier gas) are potentially flammable and explosive, it is necessary, from a practical viewpoint, to operate at concentrations outside the flammable and explosive limits of the aromatic hydrocarbon being employed. Generally, concentrations between about 1% and about 15% by volume are desirably employed.

The relative proportions of reactants generally can range from about 1 to 5 moles of nitrogen dioxide per mole of aromatic hydrocarbon and, preferably, a ratio of about 2 to 3:1 is used.

The present process is suited to either batch or continuous operations. Continuous operations can involve recirculation of the effluent stream unreacted aromatic hydrocarbon and nitrogen dioxide following isolation of the nitrated aromatic hydrocarbon product. Additional reactants—aromatic hydrocarbon and nitrogen dioxide—can then be charged to the reactor along with the recirculated stream to continue the process in a subsequent and continuous reaction. It will be noted that the substantial absence of side reactions such as, for example, the thermal decomposition of nitrogen dioxide and undesired by-product formation advantageously facilitates such continuous operations in that extensive purification of the effluent stream is not required and, as previously noted, the cost and complexity of reoxidation of the nitric oxide to nitrogen dioxide is substantially reduced or eliminated altogether.

The nitrated aromatic hydrocarbons produced during the course of the vapor phase reaction can be collected in a suitable chilled container, and purified by any appropriate method and means known to the art such as, for example, distillation and crystallization. Fractional crystallization in accordance with conventional procedures may be conveniently employed for the purification of p-nitrotoluene, m.p. 55° C., when toluene is employed as the reactant or starting material.

The recovered unreacted reactants, due to the substantial absence of side-reactions to produce undesired by-products, are easily recycled to the reactor for further processing.

The following specific examples illustrating the best presently-known methods of practicing this invention are described in detail in order to facilitate a clear understanding of the invention. It should be understood, however, that the detailed expositions of the application of the invention while indicating preferred embodiments, are given by way of illustration only and are not to be construed as limiting the invention since various changes and modifications within the spirit of the invention will become apparent to those skilled in the art from this detailed description.

EXAMPLES 1–5

A stainless steel tube 40.64 cm (16 inches) in length and 2.54 cm (1-inch) outside diameter, packed with a 35.56 cm (14-inch) bed of molecular sieve catalyst was employed as the reactor. The catalyst, unless specified otherwise, was pretreated with nitrogen dioxide at operating conditions (in the absence of the aromatic compounds) to the saturation point, usually from about 5 minutes to about 1 hour.

A stream of aromatic hydrocarbon was preheated and charged to the reactor tube in a humidified or water-containing stream of air. The nitrating agent, nitrogen dioxide unless otherwise specified, in a nitrogen or 10° C./min. The parameters and results are tabulated in Table 1.

TABLE 1

| | CATALYST[1] | | | AROMATIC HYDROCARBON, R—C$_6$H$_5$ | | | | |
|---|---|---|---|---|---|---|---|---|
| | | | Pretreat. | | | | | Carrier Gas[4] |
| EXAMPLE | Type | SiO$_2$/Al$_2$O$_3$ molar ratio | Time min. | R | Flow Rate ml/min. | g, moles | Conc. vol. % | Temp. °C. | Flow Rate ml/min. |
| 1 | Silica/alumina | 7.25/1 | 5 | H | 77.59 | 41.9, 0.54 | 8.6 | 30 | 500.0 |
| 2 | Silica/alumina | " | 2 | " | 82.77 | 40.4, 0.52 | 9.2 | " | " |
| 3 | Zeolon 900 H[7] | 10/1 | — | CH$_3$ | 34.66 | 31.3, 0.34 | 4.5 | 20 | — |
| 4 | Zeolon 900 H[9] | " | — | " | 42.19 | 38.1, 0.41 | 4.1 | " | — |
| 5 | Zeolon 900 H[10] | " | — | " | 35.29 | 45.6, 0.50 | 7.3 | " | — |

| | NITRATING AGENT[2] | | | | Carrier Gas[5] | NITRATING AGENT/ |
|---|---|---|---|---|---|---|
| EXAMPLE | Flow Rate ml/min. | g, moles | Conc. vol. % | Temp. °C. | Flow Rate ml/min. | AROMATIC COMPOUND molar ratio |
| 1 | 145.14 | 46.2, 1.00 | 16.1 | 15 | 69.0 | 1.85 |
| 2 | 135.15 | 38.8, 0.84 | 15.1 | " | " | 1.62 |
| 3 | 83.38 | 37.7, 0.82 | 10.8 | 14.5 | 37.0[4] | 2.41 |
| 4 | 145.58 | 62.8, 1.37 | 16.8 | " | 55.0[4] | 3.34 |
| 5 | 112.74 | 72.9, 1.58 | 23.4 | " | 55.0[4] | 3.16 |

| | WATER | | | | Carrier Gas[4] | REACTION CONDITIONS | | |
|---|---|---|---|---|---|---|---|---|
| EXAMPLE | Flow Rate ml/min. | g, moles | Conc. vol. % | Temp. °C. | Flow Rate ml/min. | Temp. °C. | Time hours | CONVERSION, %[3] |
| 1 | 12.04 | 1.5, 0.083 | 1.3 | 80 | 98 | 150 | 2.6 | 92.4 |
| 2 | 11.38 | 1.3, 0.072 | 1.3 | " | " | 130 | 2.3 | 70.5 |
| 3 | 43.44 | 7.7, 0.43 | 5.7 | 53 | 570 | 166[8] | 3.7 | 22.9 |
| 4 | 54.59 | 9.6, 0.53 | 6.3 | " | " | " | 3.5 | 30.7 |
| 5 | 18.01 | 4.6, 0.26 | 3.7 | " | 260 | " | 5.25 | 19.0 |

| | PRODUCTS, % | | | | | MATERIAL BALANCE | | |
|---|---|---|---|---|---|---|---|---|
| | R—C$_6$H$_4$—NO$_2$ | | | | | g | | |
| | | R = CH$_3$ | | | | | | |
| EXAMPLE | R = H | ortho | meta | para | Unidentified by | In | Out | % |
| 1 | 92.4 | — | — | — | — | 89.6 | 88.6 | 98.9 |
| 2 | 70.5 | — | — | — | — | 80.5 | 72.6 | 90.2 |
| 3 | — | 9.8 | 0.8 | 7.6 | 4.7 | 76.7 | 62.6 | 81.6 |
| 4 | — | 12.3 | 1.3 | 10.5 | 6.6 | 110.5 | 102.1 | 92.4 |
| 5 | — | 6.7 | 0.6 | 7.4 | 4.3 | 123.1 | 117.1 | 95.1 |

[1] Pretreated for the indicated period of time with nitrogen dioxide at operating conditions (in the absence of the aromatic hydrocarbon) unless specified otherwise.
[2] Nitrogen dioxide (M.W., 46) unless specified otherwise.
[3] Based on the aromatic hydrocarbon.
[4] Air
[5] Nitrogen
[6] A silica/alumina composition (SiO$_2$/Al$_2$O$_3$ molar ratio - 7.5/1) available from Strem Chemicals, Inc., Newburyport, Massachusetts 01950.
[7] Dried in an oven at 160° C. for 20 hours and cooled in air.
[8] Wall temperature. Temperature at the center of the reactor increased at an average rate of 1.5° C./min. to a maximum of 277° C. at 77 minutes of elapsed reaction time and thereafter returned to 168° C. at the end of the reaction period at an average rate of 0.8° C./min.
[9] Catalyst from Example 3 was purged with nitrogen for 1 hour at 200° C.
[10] Catalyst from Example 4 was purged with nitrogen for 5 hours at 200° C.

air carrier stream (as indicated) was mixed with the aromatic hydrocarbon/air stream shortly before contact with the heated catalyst.

The products were collected in a series of three chilled containers, the first of which was chilled in an ice water bath and the second and third of which were chilled in dry ice baths. Analyses were performed by gas chromatography on a Varian Associates Model 3700 instrument using a 1.83-meter (6-ft.) by 0.32-cm (0.125-inch) outside diameter column, packed with 0.5 percent phosphoric acid on 5/95 weight percent SP-1000/Chromosorb G [carboxylic acid terminated poly(ethylene nitroterephthalate) from poly(ethylene glycol), M.W., 20,000, and nitroterephthalic acid, Supelco, Inc., Bellefonte, PA 16823/diatomaceous earth, Johns-Manville Products Corp., Manville, N.J. 08835] and programmed from 90° C. to 210° C. at a program rate of Thus, it is apparent that there has been provided, in accordance with the present invention, a process that fully satisfies the objects and advantages set forth hereinabove. While the invention has been described with respect to various specific examples and embodiments thereof, it is understood that the invention is not limited thereto and that many alternatives, modifications, and variations will be apparent to those skilled in the art in light of the foregoing description. Accordingly, it is intended to embrace all such alternatives, modifications, and variations as fall within the spirit and broad scope of the invention.

What is claimed is:

1. A process for the vapor phase nitration of aromatic hydrocarbons selected from the group consisting of benzene and toluene which process comprises contacting the aromatic hydrocarbon with a nitrating agent in the vapor phase in the presence of a molecular sieve catalyst at a temperature between about 80° C. and about 190° C.

2. The process of claim 1 wherein the nitrating agent is nitrogen dioxide.

3. The process of claim 1 wherein the nitrating agent is admixed with a carrier gas prior to reaction with the aromatic hydrocarbon.

4. The process of claim 3 wherein the carrier gas is nitrogen.

5. The process of claim 1 wherein the molecular sieve catalyst is conditioned by pretreatment with nitrating agent.

6. The process of claim 5 wherein the pretreatment is carried out for about 1 minute to about 1 hour.

7. The process of claim 1 wherein the vapor phase reaction is carried out at temperatures ranging from about 150° C. to about 175° C.

8. The process of claim 1 wherein about 1 to about 5 moles of nitrating agent are used per mole of aromatic hydrocarbon.

9. The process of claim 1 wherein the concentration of the aromatic hydrocarbon in the feed mixture is between about 1% and about 15% by volume.

10. The process of claim 1 wherein the aromatic hydrocarbon is admixed with a carrier gas prior to reaction with the nitrating agent.

11. The process of claim 10 wherein the carrier gas is an oxygen-containing gas.

12. The process of claim 11 wherein the oxygen-containing gas is air.

13. The process of claim 1 wherein water vapor is admixed with the feed mixture prior to reaction between the aromatic hydrocarbon and the nitrating agent.

14. The process of claim 13 wherein the water vapor is present in the feed mixture in a concentration ranging from nominal amounts up to about 15% by volume.

15. The process of claim 1 wherein the aromatic hydrocarbon is benzene, the nitrating agent is nitrogen dioxide, the molar ratio of nitrogen dioxide to benzene is from about 1 to 5:1, and the temperature ranges from about 150° C. to about 175° C.

* * * * *